(12) United States Patent
Aitchison

(10) Patent No.: US 11,274,393 B2
(45) Date of Patent: Mar. 15, 2022

(54) PIEZORESPONSIVE TEXTILE INCORPORATING GRAPHENE

(71) Applicant: IMAGINE INTELLIGENT MATERIALS LTD, Sydney (AU)

(72) Inventor: Phillip Aitchison, Sydney (AU)

(73) Assignee: IMAGINE INTELLIGENT MATERIALS LTD, Sydney (AU)

( * ) Notice: Subject to any disclaimer, the term of this patent is extended or adjusted under 35 U.S.C. 154(b) by 60 days.

(21) Appl. No.: 16/494,204

(22) PCT Filed: Mar. 13, 2018

(86) PCT No.: PCT/AU2018/050227
§ 371 (c)(1),
(2) Date: Sep. 13, 2019

(87) PCT Pub. No.: WO2018/165704
PCT Pub. Date: Sep. 20, 2018

(65) Prior Publication Data
US 2020/0011006 A1    Jan. 9, 2020

(30) Foreign Application Priority Data

Mar. 13, 2017 (AU) ................................. 2017900867

(51) Int. Cl.
| G01L 1/00 | (2006.01) |
| D06M 11/74 | (2006.01) |
| A61B 5/00 | (2006.01) |
| G01B 7/16 | (2006.01) |
| G01L 1/22 | (2006.01) |

(52) U.S. Cl.
CPC ........... *D06M 11/74* (2013.01); *A61B 5/6804* (2013.01); *G01B 7/18* (2013.01); *G01L 1/22* (2013.01); *A61B 2562/0247* (2013.01); *A61B 2562/0261* (2013.01); *D06N 2209/041* (2013.01); *D10B 2401/18* (2013.01)

(58) Field of Classification Search
CPC ................. D06M 11/74; A61B 5/6804; A61B 2562/0247; A61B 2562/0261; G01B 7/18; G01L 1/22; D06N 2209/041; D10B 2401/18
See application file for complete search history.

(56) References Cited

U.S. PATENT DOCUMENTS

| 10,337,124 B2* | 7/2019 | Egan ........................ D01F 1/10 |
| 2015/0061460 A1* | 3/2015 | Bae .......................... H02N 1/04 |
| | | 310/310 |

(Continued)

FOREIGN PATENT DOCUMENTS

CN          105951427 A       9/2016

OTHER PUBLICATIONS

Fabrication of a graphene coated nonwoven textile for industrial applications https://pubs.rsc.org/en/content/articlelanding/ra/2016/c6ra15190f#!divAbstract (Year: 2015).*

(Continued)

*Primary Examiner* — Max H Noori
(74) *Attorney, Agent, or Firm* — AEON Law, PLLC; Adam L. K. Philipp; David V. H. Cohen

(57) ABSTRACT

An electrically conductive textile containing graphene that undergoes a change in electrical resistance when deformed.

8 Claims, 1 Drawing Sheet

(56) References Cited

U.S. PATENT DOCUMENTS

| | | | |
|---|---|---|---|
| 2015/0129276 A1* | 5/2015 | Shumaker | H01B 3/28 |
| | | | 174/69 |
| 2018/0171514 A1* | 6/2018 | Cobanoglu | D03D 15/47 |
| 2019/0040548 A1* | 2/2019 | Aitchison | G01M 3/40 |
| 2020/0191549 A1* | 6/2020 | Aitchison | G01D 5/24 |
| 2020/0282244 A1* | 9/2020 | Florence | G01L 5/047 |
| 2021/0048750 A1* | 2/2021 | Craciun | H01L 21/02428 |

OTHER PUBLICATIONS

"Environmentally-friendly graphene textiles could enable wearable electronics", published on Nov. 25, 2016, retrieved from internet on Jun. 18, 2018, URL: http://www.cam.ac. uk/research/news/ environmentally-friendly-graphene-textiles-couldenable-wearable-electronics.

Lu Z. et al., "Highly Conductive Graphene-coated Silk Fabricated via a Repeated Coating-Reduction Approach", Journal of Materials Chemistry C, 3, Apr. 7, 2015, pp. 4265-4268.Supplementary materials retrieved from internet on Jun. 18, 2018, URL:http://www.rsc.org/suppdata/c5/tc/c5tc00917k/c5tc00917k1.pdf.

Park J. J. et al., "Highly Stretchable and Wearable Graphene Strain Sensors with Controllable Sensitivity for Human Motion Monitoring", ACS Applied Materials & Interfaces, Mar. 4, 2015, 7, pp. 6317-6324.

\* cited by examiner

PIEZORESPONSIVE TEXTILE INCORPORATING GRAPHENE

TECHNICAL FIELD

The invention relates to the field of Piezoresponsive textiles. In particular, the invention relates to an electrically conducting textile that changes electrical properties when strained.

BACKGROUND OF THE INVENTION

Strain and gauges are widely used. When used as pressure gauges they can be highly precise and can be made by many means from many materials. Typically, they are stand-alone electrical devices using a material or arrangement of materials that undergo a change in electrical properties when pressure is applied. The change in electrical property is usually resistance, capacitance or inductance.

Deformation of a material changes the relative positions of the components of the material, resulting in strain. Such deformation may be elastic or inelastic, a combination of both or only partially elastic, with some permanent deformation occurring with each deformation. The deformation may be compressive or extensive and may occur in any or all of the three physical dimensions. In practice compression of a sheet of material by applying a force perpendicular to the plane of the sheet makes the sheet thinner in the area of applied force. Stretching a sheet of material that can be compressed in the plane of the sheet often also makes it thinner. Various individual or combinations of these deformations can be used to measure strain.

Elasticity is formally measured as the 'modulus of elasticity' (also known as tensile modulus and Young's modulus). Elastic reversibility is the degree to which an object recovers its original shape after deformation. Generally, elasticity is regarded as reversible if the object remains fit for purpose after elastic deformation. In strain sensors, non-elastic deformation can be compensated for.

Strain gauges often use a deformable electrical conductor, such as a thin metal wire or foil in a complex pattern to maximise sensitivity bonded to a flexible or stretchable insulating sheet. When the insulator is stretched, the electrical conductor is deformed and its resistance changes. If the electrical conductor is stretched the electrical pathway becomes narrower and longer, increasing resistance. If compressed the electrical pathway becomes shorter and wider, decreasing resistance. This effect can be described as Piezoresistance. Such two-dimensional strain gauges can be arranged on a membrane to act as a pressure sensor.

Piezoresistance can be used to measure variations in strain (and by inclusion pressure). Semiconductors, such as silicon and germanium are well known Piezoresistive materials. They undergo a large change in resistance with strain and make excellent high precision and high sensitivity pressure sensors.

Electrical resistance can be reported in many ways. For electrical conduction in a thin sheet, the unit "Ohms per square" ("Ohm/sq" or "Ohm/□") is often used and referred to as "sheet resistance". This unit is of practical advantage in that it reflects a desired outcome regardless of how the material being measured is constructed. For example, two sheets of electrical conductor may have different specific resistances but may nevertheless give the same, desirable sheet resistance if present in different thicknesses. Sheet resistance is normally applied to uniform thickness films, but can also be applied to non-uniform sheets of conductors, such as a textile.

Measurement of resistance, capacitance and inductance can be achieved by many means. In analogue strain gauges a Wheatstone bridge or a potentiometer can be used to determine an unknown resistance. Modern digital equipment and semiconductor technology allows easy, accurate and relatively low cost measuring equipment to measure one or more electrical parameters.

Strain sensing over large areas requires materials that are robust and relatively inexpensive. Semiconductor technology is inappropriate. Strain sensors using conductive, stretchable polymers, such as rubbers are well known. Velostat® is one commercially available example where an electrically insulating polyolefin has had electrically conducting carbon particles (carbon black) added to make it electrically conductive. When the sheet is stretched, it changes resistance allowing it to be used as a strain sensor. The nature of its structure means that when pressure is applied to the sheet in a direction perpendicular to the sheet, a change in resistance occurs in the direction of the applied pressure, but not in directions perpendicular to the applied pressure (in-plane or sheet resistance).

Textiles, also known as fabrics or cloths, are flexible material consisting of a network of natural and/or artificial fibres. A wide range of materials are used as fibres dependant on the desired properties and application Textiles can be formed from fibres by many methods, including: weaving, knitting, knotting, braiding and non-woven overlay techniques where further steps, such as inter-tangling (e.g. needle punch, felting, hydro-entanglement, spun lacing, water needling) and can include various steps to improve the desired properties, such as carding and heat bonding.

Conductive textiles can be made from electrically conductive fibres, such as: metals; conductive polymers (e.g. polypyrole); carbon-filled polymer fibres and; metal-filled polymer fibres. Further, the textiles can be made from coated fibres, where a non-conductive polymer (polyolefin or natural fibre) is coated with an electrically conductive layer, such as those noted here and then the fibres are made into a textile. In some cases, the conductive textile is made from a mixture of conductive and non-conductive fibres depending on the desired properties. Alternatively, textiles can be made conductive by coating the textile with a conductive material.

Electrically conductive textiles are typically expensive in comparison to non-conductive textiles, thus limiting the size of individual applications and the breadth of applications. Further most conductive textiles do not have a significant Piezoresistive effect. And even more limiting, materials that do exhibit a Piezoresistive effect only do so in the direction of applied pressure or strain.

There are many industrial uses of textiles. Sometimes referred to as 'technical textiles' these range from civil engineering and related geotechnical applications, to construction, manufacturing and automotive. Generally, they are regarded as non-aesthetic and form a component of another part. Very few cost-effective options are available for large-scale electrically conductive textiles.

Textiles for clothing and medical applications with a strain and or pressure response usually rely on complex electrical components being embedded in the textile, or attached to the textile after the item has been formed. In some cases, the sensor is printed onto the textile using conductive inks. In such cases the sensor is a discreet object and not an inherent part of the textile.

Accordingly, it is an object of the invention to provide a deformable material for use as part of a strain sensing system that ameliorates at least some of the problems associated with the prior art.

SUMMARY OF THE INVENTION

According to a first aspect of the invention, there is provided an electrically conductive textile incorporating graphene that changes electrical resistance when deformed.

In particular, the conductive textile incorporating graphene exhibits a Piezoresistive effect in all three dimensions and is capable of use as a pressure sensor or a strain sensor.

Textiles, also known as fabrics or cloths, are flexible material consisting of a network of natural and/or artificial fibres. A wide range of materials are used as fibres dependent on the desired properties and application Textiles can be formed from fibres by many methods, including: weaving, knitting, knotting, braiding and non-woven overlay techniques where further steps, such as inter-tangling (e.g. needle punch, felting, hydro-entanglement, spun lacing, water needling) and can include various steps to improve the desired properties, such as carding and heat bonding.

Conductive textiles can be made from electrically conductive fibres, such as: metals; conductive polymers (e.g. polypyrole); carbon-filled polymer fibres and; metal-filled polymer fibres. Further, the textiles can be made from coated fibres, where a non-conductive polymer (polyolefin or natural fibre) is coated with an electrically conductive layer, such as those noted here and then the fibres are made into a textile. In some cases, the conductive textile is made from a mixture of conductive and non-conductive fibres depending on the desired properties. Alternatively, textiles can be made conductive by coating the textile with a conductive material.

Electrically conductive textiles are typically expensive in comparison to non-conductive textiles, thus limiting the size of individual applications and the breadth of applications. Further most conductive textiles do not have a significant Piezoresistive effect. And even more limiting, materials that do exhibit a Piezoresistive effect only do so in the direction of applied pressure or strain.

There are many industrial uses of textiles. Sometimes referred to as 'technical textiles' these range from civil engineering and related geotechnical applications, to construction, manufacturing and automotive. Generally, they are regarded as non-aesthetic and form a component of another part. Very few cost-effective options are available for large-scale electrically conductive textiles.

Textiles for clothing and medical applications with a strain and or pressure response usually rely on complex electrical components being embedded in the textile or attached to the textile after the item has been formed. In some cases, the sensor is printed onto the textile using conductive inks. In such cases the sensor is a discrete object and not an inherent part of the textile.

Graphene is essentially an individual layer of graphite and can be formed by many routes, including "top-down" approaches such as mechanical or electrochemical exfoliation of graphite, chemical oxidation of graphite and exfoliation as graphene oxide followed by partial or complete reduction to graphene and "bottom-up" approaches such as growth from gases or plasmas on substrates or catalysts. The character of the graphene can vary from nearly atomically perfect single layers through two-layer, few-layer and multi-layer graphene all the way up a scale of number of layers which culminates in large agglomerates similar to ultra-fine graphite. Graphene has a high aspect ratio, being ultimately only one atomic layer thick (less than one nanometre) and typically hundreds of nanometres to hundreds of microns in the planar directions. Thus, graphene is referred to as being a two-dimensional (2D) material. Graphene is an excellent electrical conductor.

Preferably, the textile undergoes an elastic deformation in the plane of the textile when subjected to strain in the plane of the textile and/or the textile undergoes an elastic deformation perpendicular to the plane of the textile when subjected to strain perpendicular to the plane of the textile. Preferably, the change in resistance is reversible.

The graphene may be applied to the textile after formation of the textile. The graphene may be applied to the textile so that graphene is distributed throughout the thickness of the textile.

The graphene may be applied to one side of the textile so that only part of the thickness of the textile contains graphene.

The graphene may be applied to fibres comprising the textile after the formation of the fibres, or alternatively the graphene may be incorporated into fibres comprising the textile.

Preferably, the fibre is electrically conductive and the textile is electrically conductive. This textile may be formed so as not to be uniformly electrically conductive. The proportion of electrically conductive fibres may be 100%, alternatively greater than 50%, alternatively greater than 10%, alternatively greater than 1%.

The invention alternatively provides a textile with a first side comprising at least one area containing graphene that is electrically conductive and a second side comprising at least one area containing graphene such that an electrical resistance can be formed between at least one of the areas on the first side and at least one of the areas on the second side and where that electrical resistance can change when the textile is deformed.

The textile may be configured such that a first area of electrical conductivity on each of the first and second side is connected to a second and third area of electrical conductivity on the respective side. The second and third areas of electrical conductivity may be used to connect electrical equipment to the first area.

The textile above, with a repeating pattern comprising a first, second and third area, may be configured such that the second and third areas are not electrically connected to each other on the textile except where a first area is interposed between the second and third areas.

An electrical circuit can be made by connection to the second and third areas and where the position of connection of the circuit creates an electrical pathway with a first resistance to a primary first area and a second resistance to a secondary first area, wherein the primary and secondary resistances are different.

Now will be described, by way of a specific, non-limiting example, a preferred embodiment of the invention with reference to the drawings.

DETAILED DESCRIPTION OF THE INVENTION

Figure 1:
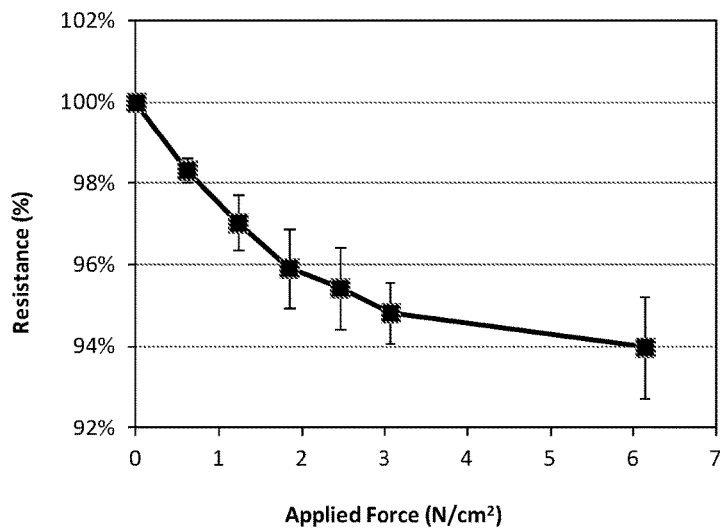
FIG. 1 is a graph showing the change in electrical resistance of a rectangle of textile sensor made from non-woven polyester coated on only one side with graphene when compressed perpendicular to the plane of the sheet.

Various forms of graphene exist. Ideal graphene is pure carbon and the best electrical conductor in the graphene family and one of the best conductors ever discovered. It is free of defects and other chemical functionality, such as oxygen. Graphene oxide (GO) is a highly oxidised form of graphene that is an electrical insulator.

Intermediary species can be referred to by various descriptions, such as partially reduced graphene oxide (prGO) or functionalised graphene, where various chemical groups are attached to the edges and/or basal planes of the graphene. This functionality allows tailoring of the electrical and physical properties of the graphene, for example to make it easier to incorporate into or onto materials, such as plastics to form composites. Incorporation of heteroatoms, where carbon atoms are replaced by other atoms, such as nitrogen and other covalently bonded atoms can also be used to tailor the properties of graphene.

Graphene can also come in various dimensions, whether it be single layers of graphene or multiple layers. Various terminologies have been used to describe the structural permutations and some attempts have been made at standardising terminology. Regardless of terminology these single-layer and multi-layer structures of graphene have useful conductivity that give rise to the properties in polymers, fibres and textiles as described here.

These various permutations of graphene are generalised here as "graphene" unless otherwise detailed and their properties described. The continuous scale from electrically conductive to electrically insulating means many forms of graphene can be used as an electrical conductor and even poorly conducting graphene can serve the purpose, especially where it's other properties make it desirable for use.

Graphene can be produced by many routes, including: anodic bonding; carbon nanotube cleavage; chemical exfoliation; chemical synthesis; chemical vapour deposition; electrochemical exfoliation; electrochemical intercalation; growth on silicon carbide; liquid phase exfoliation; micromechanical cleavage; microwave exfoliation; molecular beam epitaxy; photo-exfoliation; precipitation from metal, and; thermal exfoliation. Some of these routes give rise to materials referred to as: chemically converted graphene; few-layer graphene; GO; graphene; graphene oxide; graphene nanoflakes; graphene nanoplatelets; graphene nanoribbons; graphene nanosheets; graphite nanoflakes; graphite nanoplatelets; graphite nanosheets; graphite oxide; LCGO; liquid crystal graphene oxide; multi-layer graphene; partially reduced graphene oxide; partially reduced graphite oxide; prGO; rGO; reduced graphene oxide; reduced graphite oxide.

Incorporation of graphene into or onto a textile can be achieved by many methods, but in each case the properties of the fibres and the textile will affect the method of incorporation. The method of incorporation will depend on the fibre and textile chemistry, graphene chemistry, graphene shape and processes used to incorporate the graphene into or onto the fibres and the process of forming a textile. For synthetic or composite fibres, preferred methods include mixing the graphene into the polymer or composite prior to forming synthetics fibres. Both natural and synthetic fibres can be coated with graphene to make a conductive fibre and textiles and textile intermediates can be coated to provide conductivity in the textile.

For dispersion of the graphene into a polymer for synthetic fibres or composite fibres the graphene can be present as a powder or as a dispersion in a fluid. Pre-dispersion of the graphene in a suitable fluid facilitates dispersion of the graphene in the polymer. Coating the graphene is preferably from a dispersion of graphene in a fluid. Methods of incorporation of graphene into the polymer can include: Melt-compounding of graphene into the polymer; in-situ polymerisation of the polymer with the graphene, and; solution blending. Whichever technique is used, it is desirable that the graphene is sufficiently dispersed to achieve electrical conductivity with a minimum of graphene.

In some cases, additives are required to reduce phase separation of the graphene and the polymer.

A preferred method is where the textile is formed from a fibre that includes graphene. The fibre is formed by melt extrusion from pellets or powders of the polymer. The graphene is added to the melt extrusion in a concentrated form dispersed in a carrier polymer, which may be the same as the bulk polymer, or may be different. The concentrated form of the graphene polymer dispersion is mixed and diluted in the melt extrusion process to obtain the desired concentration of graphene in the fibres. In another embodiment, the concentrated form of the graphene is dispersed in a fluid, such as: oil, solvent or water.

Electrical measurements rely on electrical conductivity to form a circuit. Sufficient conductivity depends on the size and length of the conductive path and the conductivity of the conductive media. This combination of variables gives a wide range over which the measurements can be effective. Tuning the measurement method to the desired outcome and conditions is required. This allows the electrical conductivity of the textile to also be tailored to the desired application and measurement methods. In some cases, the electrical conductivity of the conductive textile can be quite low, such as where the measurement voltage is high, the change in resistance is large and the circuit path is short.

In some embodiments, the resistance of a circuit is measured, in others it is the capacitance or inductance.

In one embodiment, natural cotton, woven, non-elastic clothing textiles were coated with a dispersion of graphene from a carrier solvent. After drying the areas coated were electrically conductive. The conductivity could be tailored to give the desired conductivity and Piezoresistive response to compression and stretch. Conductivity and Piezoresistive response could be controlled by the amount of graphene applied and the penetration of the graphene into the textile. The greater the thickness of the penetration of the graphene into the textile the greater the Piezoresistive response.

It is hypothesised that the three-dimensional textile structure provides a scaffold, which when coated with the appropriate graphene particles provides a mechanism by which compression of the textile perpendicular to the textile sheet direction leads to greater fibre to fibre contact across the thickness of the textile in the direction of compression and thus a greater number of electrically conductive pathways for electrical current to flow and thus a lower resistance being measured. This change in resistance can be measure both in the direction of the applied compression (across the thickness of the textile) and in the plane of the textile (perpendicular to the direction of the applied compression).

In another embodiment, thick, low density, non-woven, felted polyester textiles were coated with aqueous polymer dispersions of graphene to form a conductive layer into the top part of one side of the textile. When compressed, the low density felted textile deformed significantly and gave a Piezoresistive response as measured across the sheet (in the plane) of the textile. As predicted by theory, the Piezoresistive response (measured as a change in voltage and converted to a resistance) showed a decrease in resistance with increasing applied force and the degree of resistive decrease was greater the larger the area of applied pressure in proportion the area of the textile.

In another embodiment, a thin coating of graphene was applied as an aqueous polymer dispersion to one side of thin elastic woven textiles. In some cases, the textile was elastic in both directions, in others the textiles were only elastic in only one direction. The graphene coating was only applied to the surface of the textile with no significant penetration of the graphene into the thickness of the textile. Stretching the textile in a direction of elasticity gave an increase in resistance proportional to the degree of stretch. Compression of the thin textile perpendicular to the plane of the textile gave only a small decrease in resistance. In this case the graphene coating is behaving like a two-dimensional strain gauge.

The present invention will now be described with reference to the following non-limiting examples.

Example 1

Squares of approximately 10 cm² of an approximately 140 g/m² melt-spun, non-woven, needle-punched polyester were coated with a dispersion of 0.05 wt. % graphene in xylene by repeatedly dipping the textile into the dispersion of graphene until the textile became black. After air drying the conductivity was measured to be approximately 2000 Ω/square.

Example 2

Strips approximately 5 cm by 2 cm of an approximately 140 g/m² melt-spun, non-woven, needle-punched polyester were coated with a dispersion of graphene oxide in water by repeatedly dipping the textile by hand into the dispersion of graphene oxide and leaving it immersed until the geotextile became dark brown. The coated textile was then treated with citric acid as a reducing agent to convert the graphene oxide to graphene. After rinsing and air drying the conductivity was measured to be 870 Ω/square.

Example 3

Graphene nanoplatelets (GNP) were made by thermal exfoliation of expandable graphite at 1050° C. in argon, followed by exfoliation by ultrasonication in water. Scanning electron microscopy (SEM) showed the platelets were approximately 1 micron in diameter and ranged from single layer up to more than 10 layers. The GNP was mixed with an aqueous acrylic binder to give a 2 wt. % graphene dispersion and blade coated onto one side of an approximately 190 g/m² melt-spun, non-woven, needle-punched polyester to give an approximately 2 wt. % coating of graphene on the textile. Electrical resistance was measure on each side of the textile as approximately 3400 Ω/square on the coated side and infinite (>20 MO) on the uncoated side. FIG. 1 shows the pressure response curve for a 4 cm by 14 cm sample of the coated textile when an area 4 cm by 4 cm was compressed across the width of the sample. It will be observed that the resistance shows a predictable relationship with the applied force.

Example 4

Figure 2:
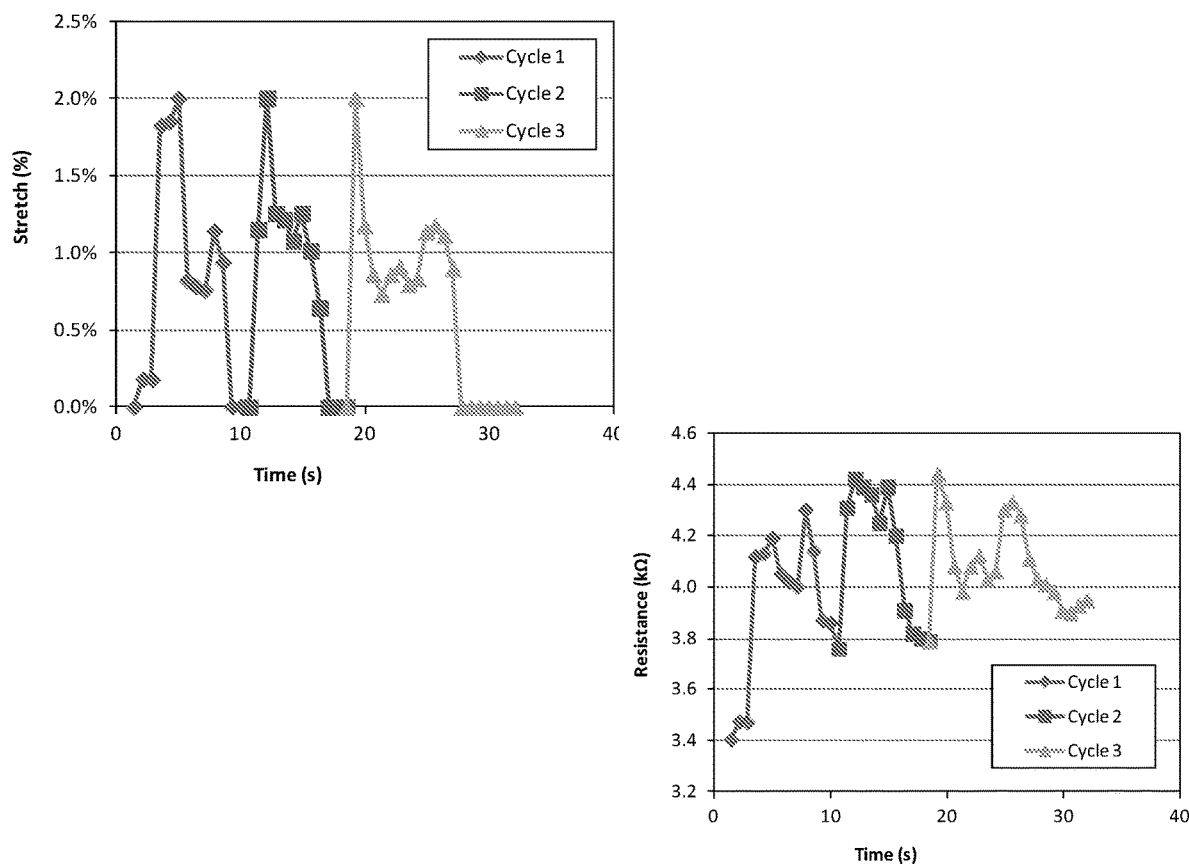
FIG. 2 shows two graphs showing an elastic textile made from elastane coated on one side with a flexible graphene coating. The change in electrical resistance (left) and the stretching (right) with time for three cycles of stretching.

A commercial elastic textile made from elastane fibres (also known as Spandex and Lycra) was blade coated on one side with a 2 wt % graphene dispersion in an aqueous acrylic binder with a cellulosic thickener. The coated area was approximately 20 cm by 2 cm. Once dried at 120° C., the graphene coating is flexible and partly elastic. The two-point resistance when measured along the length of the coated area was approximately 3.5 kΩ. The highly elastic nature of the elastane meant that the starting point for any separate series of resistance measurements was different. Small amounts of stretching (<5%) of the elastane gave mostly reversible changes in resistance with approximately 300Ω increase in resistance per 1% stretch. FIG. 2 shows the relationship observed between stretching and resistance change, where it will be observed that the relationship between stretch amount and electrical resistance appears to be predictable.

It will be appreciated by those skilled in the art that the above described embodiment is merely one example of how the inventive concept can be implemented. It will be understood that other embodiments may be conceived that, while differing in their detail, nevertheless fall within the same inventive concept and represent the same invention.

The invention claimed is:

1. An electrically conductive textile containing graphene that changes electrical resistance when deformed, wherein the graphene has been applied to fibres comprising the textile after the formation of the fibres, wherein the fibres are electrically conductive and the textile is electrically conductive, and wherein the fibres are not uniformly electrically conductive.

2. The textile according to claim 1, wherein approximately 100% of the fibres are electrically conductive.

3. The textile according to claim 1, wherein greater than 50% of the fibres are electrically conductive.

4. The textile according to claim 1, wherein greater than 10% of the fibres are electrically conductive.

5. The textile according to claim 1, wherein greater than 1% of the fibres are electrically conductive.

6. An electrically conductive textile containing graphene that changes electrical resistance when deformed, wherein said textile comprising one or more areas containing graphene that are electrically conductive, wherein said areas change electrical resistance when deformed, and wherein a first area of electrical conductivity is electrically connected to a second and third area of electrical conductivity; and wherein said first area of electrical conductivity changes resistance with deformation; and wherein said second and third areas are adapted to be used to connect electrical equipment to the first area.

7. The textile according to claim 6, wherein said first, second and third areas comprise a repeating pattern, wherein said second and third areas are only electrically connected to each other where said first area is interposed between the second and third areas.

8. The textile incorporating a pattern according to claim 7, wherein an electrical circuit can be made via electrical connection of more than one first area to one of said second and third areas; and wherein the position of connection of the circuit in said areas is selected so as to create an electrical pathway with a first resistance to a first area and a second resistance to another first area wherein said first and second resistances are different.

* * * * *